United States Patent [19]
Visser et al.

[11] Patent Number: 5,813,764
[45] Date of Patent: Sep. 29, 1998

[54] CATALYTIC DIFFERENTIAL CALORIMETRIC GAS SENSOR

[75] Inventors: Jacobus Hendrik Visser, Southfield; Chaitanya Kumar Narula, Ann Arbor; Margherita Zanini-Fisher, Bloomfield Township, all of Mich.

[73] Assignee: Ford Global Technologies, Inc., Dearborn, Mich.

[21] Appl. No.: 940,144

[22] Filed: Sep. 29, 1997

Related U.S. Application Data

[62] Division of Ser. No. 311,299, Sep. 23, 1994, Pat. No. 5,707,148.

[51] Int. Cl.$^6$ ............................ G01N 25/20; G01K 17/00
[52] U.S. Cl. ................... 374/12; 374/10; 374/31; 73/25.05; 422/51; 422/95; 431/76; 204/424; 60/276
[58] Field of Search ................... 374/10, 12, 31, 374/36; 60/276; 422/51, 95, 94; 431/76; 502/407, 415, 326; 204/424; 73/25.03, 25.05

[56] References Cited

U.S. PATENT DOCUMENTS

| | | | |
|---|---|---|---|
| 4,355,056 | 10/1982 | Dalla Betta et al. | 427/126.4 |
| 4,378,385 | 3/1983 | Hughes | 427/126.3 |
| 4,560,585 | 12/1985 | Khilnani | 427/103 |
| 4,579,751 | 4/1986 | Foster | 427/54.1 |
| 4,699,892 | 10/1987 | Suzuki | 502/4 |
| 4,839,327 | 6/1989 | Haruta et al. | 502/243 |
| 5,134,107 | 7/1992 | Narula | 502/303 |
| 5,210,062 | 5/1993 | Narula et al. | 502/304 |
| 5,234,881 | 8/1993 | Narula et al. | 502/262 |
| 5,265,417 | 11/1993 | Visser et al. | 60/274 |
| 5,292,801 | 3/1994 | Avnir et al. | 525/54.1 |
| 5,340,548 | 8/1994 | Abe et al. | 422/177 |
| 5,431,012 | 7/1995 | Narula et al. | 60/276 |
| 5,451,371 | 9/1995 | Zanini-Fisher et al. | 422/51 |
| 5,480,622 | 1/1996 | Narula et al. | 422/174 |

FOREIGN PATENT DOCUMENTS

| | | |
|---|---|---|
| 3839414A1 | 5/1990 | Germany . |
| 55-156850 | 12/1980 | Japan . |
| 0255649 | 10/1988 | Japan ..................................... 374/10 |
| 1145561 | 6/1989 | Japan . |
| 2238617 | 11/1989 | United Kingdom . |
| WO9303840 | 3/1993 | WIPO . |

OTHER PUBLICATIONS

"Sol–Gel Thin Film Formation", by C.J. Brinker et al, Journal of the Ceramic Society of Japan, vol. 99–843, Oct. 1991.

"Large Clusters and Colloids. Metals in the Embryonic State", by Gunter Schmid, Chem. Rev. 1992, 1709–1727. No Month.

"Ethanol Gas Sensing Properties of SnO2–based Thin–film Sensors Prepared by the Sol–gel Process", by Sung–Soon Park et al, Materials Letters, Oct. 1993, No. 6.

"The Si–Planar–Pellistor Array, a Detection Unit for Combustible Gases", by M. Gall, Sensors & Actuators, Oct. 1993, Nos. 1/3.

"Fabrication and Proeprties of a Si–Based High Sensitivity Microcalorimetric Gas Sensor", by. M. Zanini et al, Jun. 1994.

"Catalytic Calorimetric Gas Sensors", by J.H. Visser et al, 5th International Meeting on Chemical Sensors, Jul. 11–14, 1994.

*Primary Examiner*—Diego F. F. Gutierrez
*Attorney, Agent, or Firm*—Lorraine S. Melotik; Roger L. May

[57] ABSTRACT

A catalytic differential gas combustible microcalorimeter sensor for monitoring the exhaust gas conversion for monitoring the exhaust gas conversion efficiency of a catalytic converter. The catalytic calorimetric sensor disclosed includes a sol-gel processed washcoat and sol-processed catalytically active metal particles. Sol-gel processing creates a washcoat with high surface area and controlled porosity which increases the sensitivity, durability, and reproducibility of the resultant sensor.

5 Claims, 3 Drawing Sheets

5,813,764

CATALYTIC DIFFERENTIAL CALORIMETRIC GAS SENSOR

This is a divisional of application Ser. No. 08/311,299, filed on Sep. 23, 1994 now U.S. Pat. No. 5,707,148.

TECHNICAL FIELD

The present invention is concerned with diagnostic methods and devices for monitoring exhaust gases generated from automotive engines.

BACKGROUND OF THE INVENTION

The Environmental Protection Agency (EPA) and the California Air Resources Board (CARB) have implemented stringent diagnostic requirements for automotive emissions. As part of their requirements, CARB has mandated on-board monitoring of the exhaust gas conversion efficiency of catalytic converters, under its On-Board Diagnostics phase 2 (OBD-II) plan.

Exhaust gas constituents (EGC) sensors have been proposed as an answer to the new regulation. One such potential EGC sensor is the catalytic calorimetric sensor.

In a catalytic calorimetric sensor combustible gases (such as hydrocarbons HC, carbon monoxide CO, hydrogen $H_2$, etc.) are oxidized with the help of a catalytic layer. The generated heat, measured as the increase in substrate temperature, results in an electrical output signal proportional to the amount of combustible gases present in the gas mixture.

Catalytic calorimetric gas sensors typically operate in the 250° to 500° C. temperature range, making them in principle applicable for automotive applications. Although generally of lower sensitivity than semiconducting-type gas sensors, catalytic calorimetric sensors appear to be considerably more stable and faster responding. However, existing catalytic calorimetric sensors have been investigated and found not suitable for automotive use because of application-oriented limitations. Such limitations have included a lack of sensitivity, restrictive detection limits and response time, susceptibility to flow and temperature variation.

These disadvantages of the prior art devices combine to limit the usefulness and applicability of catalytic calorimetric gas sensors.

U.S. Pat. No. 4,355,056 discloses a method of manufacturing a differential thermocouple combustible sensor which makes the sensor relatively insensitive to sulfur poisoning. The catalytic thermocouple junction of a catalytic/non-catalytic junction pair is formed by coating it with a gel to increase the surface area and then with a chloroplatinic acid solution to make it catalytic. The catalytic junction is then treated with $H_2S$ to achieve a high catalyst surface area. In this patent, the noble metal catalyst is applied from a solution, which results in large particle sizes and an accordingly small number of catalytic sites, the resulting sensor lacks sensitivity.

The prior art suffers from a lack of sensitivity. There thus exists a need for a more sensitive gas sensor which also exhibits durability.

SUMMARY OF THE INVENTION

The present invention relates to a sensitivity-enhanced catalytic calorimetric sensor.

The present invention discloses a catalytic calorimetric sensor comprising: a substrate, a temperature measuring layer and a sol-gel processed catalytic layer.

The invention also discloses a catalytic calorimetric sensor comprising: a substrate, a temperature measuring layer and a catalytic layer which comprises a sol-gel processed washcoat and a plurality of catalytically active metal particles loaded thereon.

An alternative embodiment of the present invention teaches a catalytic calorimetric gas sensor, comprising: a substrate, a temperature measuring layer and a catalytic layer which comprises a sol-gel processed washcoat and a plurality of sol-gel processed catalytically active metal particles deposited on the washcoat.

The present invention also discloses a silicon micromachining method for producing a catalytic calorimetric gas sensor to yield a highly reproducible and sensitive combustible gas sensor.

Lastly, the present invention discloses a method to maximize deposition of the catalytically active metal particles in the pores of the washcoat. This method reduces agglomeration of the metal particles while making high surface area metal particles available for catalytic reactions.

Sol-gel processed alumina/silica washcoats are beneficial for use with sensors due to the high surface area and controlled porosity that can be achieved.

The use of a sol-gel processed catalytically active metal particles results in a catalyst comprising smaller metal particles of better uniformity than those provided from conventional coating systems, such as sputtering and the like.

It is an object of the present invention to provide a catalytic calorimetric gas sensor, where some or all of the catalytic layer is processed using a sol-gel technique to create a sensor having an increased number of active catalytic sites for catalytic oxidation of the combustible gas molecules.

It is also an object of the present invention to provide a sensitivity-enhanced calorimetric gas sensor using a sol-gel technique to process some or all of the catalytic layer.

It is another object of the present invention to provide a catalytic calorimetric gas sensor that is more durable and more easy to manufacture.

It is a further object of the present invention to provide a method for fabricating catalytic calorimetric sensors with lower power consumption at potentially lower manufacturing costs using silicon micromachining.

The above objects and other objects, features and advantages of the present invention are readily apparent from the detailed description of the best mode for carrying out the invention when taken in connection with the accompanying drawings.

BEST MODE FOR CARRYING OUT THE INVENTION

The present invention generally relates to the application of a sol-gel processed, high-surface area alumina and/or silica washcoat and catalytically active metals impregnated thereon to fabricate the catalytic layer of a combustible gas sensor. Sol-gel processed alumina-silica materials are beneficial in sensor applications because such materials can be processed easily and have desired properties such as high-surface area and controlled porosity resulting in a sensor with increased sensitivity and durability.

Sensitivity is determined by two factors, the rate of gas diffusion and the rate of oxidation. In this two step process, the gas molecules are transported by diffusion to the catalytic layer, and then oxidized. Sol-gel processing provides a way to increase the number of catalytic active sites and thus increase the rate of oxidation for certain specified exhaust gases. However, in the beginning stages of sensor usage, the increased number of catalytic sites may not drastically increase the sensitivity of the sensor. It is believed that initially, once a given amount of active sites are created, the marginal utility of each subsequent active site decreases. One theory is that during this initial period, because of the large number of active sites created, the rate limiting step becomes the rate of gas diffusion and not the rate of oxidation. Nonetheless, over a period of years the number of catalytic sites decreases as a result of poisoning of the catalyst and thermal sintering. Thus by increasing the number of catalytic sites produced, the enhanced level of sensitivity will be sustained over the course of operation. Accordingly, the durability and life of the sensor significantly increases through the use of sol-gel processed catalytic sensors.

It is further believed that the instant solgel technique provides a catalytic layer with an increased number of active catalytic sites compared to those provided from conventional coating systems. This then may allow the formed coating to be thinner, resulting in a catalytic calorimetric sensor having an enhanced sensitivity.

Figure 1:
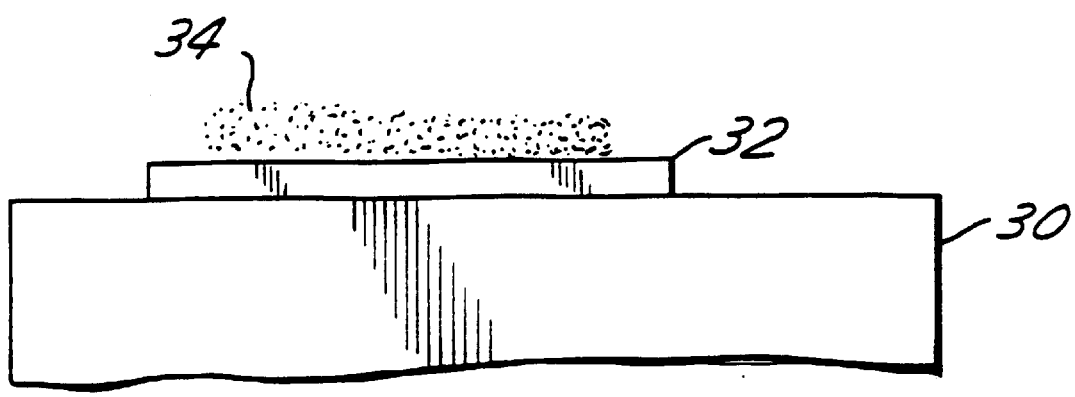
FIG. 1 is a schematic representation of the catalytic calorimetric sensor utilized in the present invention.

A schematic diagram of a catalytic calorimetric sensor is shown in FIG. 1. It consists of a substrate 30. On top of this substrate is a layer to measure the temperature 32. The temperature measuring device which comprises the temperature measuring layer can be selected from the group consisting of a thermocouple, a temperature dependent metal resistor, a temperature dependent semiconductor resistor, a p-n junction semiconductor and a thermopile. This layer can be made by sputtering, screen printing, sol-gel process, etc. Additionally, a catalytic layer 34 is placed on top of the temperature measuring layer to enable the oxidation of combustible gases in the 300°–500° C. temperature range. The substrate should be as thin as possible. The substrate should preferably have a thickness in the range between 500 to 1000 nm. The substrate should also be comprised of materials with a low thermal conductivity, such as a ceramic or a silicon micromachined structure. Examples of suitable ceramic materials include aluminum oxide, silicon oxide, polysilicon, silicon nitride or combinations thereof.

Figure 2:
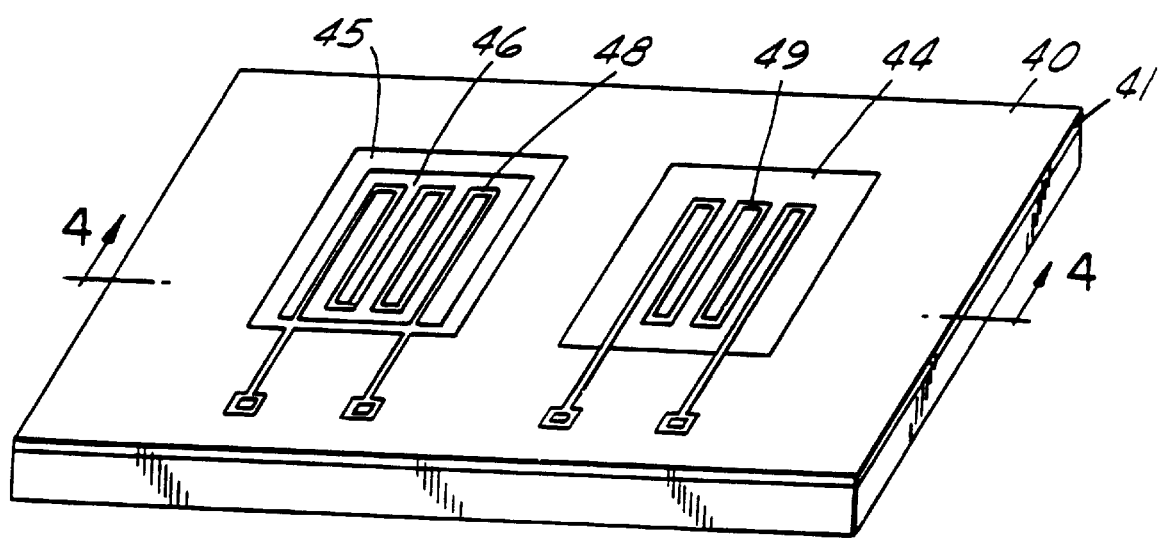
FIG. 2 is a perspective view of the microcalorimeter design used in the invention herein described.
Figure 3:
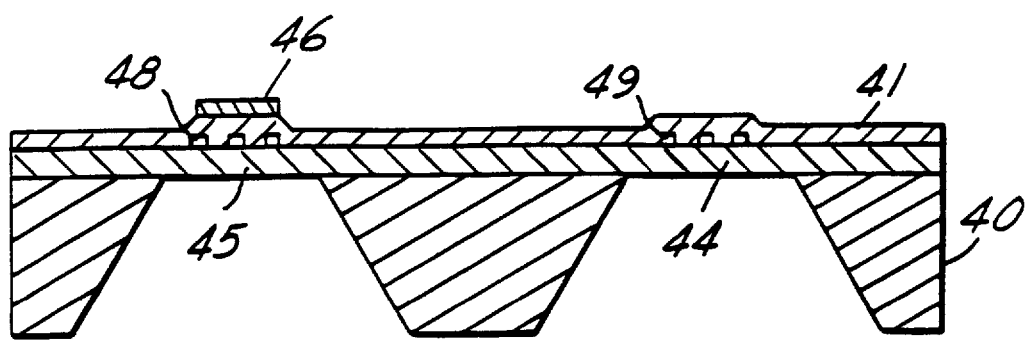
FIG. 3 is a cross-section of FIG. 2 taken along lines 4—4.

Below we will also discuss the most preferred embodiment, a differential microcalorimeter structure as shown in FIGS. 2 and 3. It is a differential microcalorimeter in which one membrane is covered with a catalytic layer and the other membrane acts as a reference to compensate for temperature fluctuations in the gas. FIG. 2 is a perspective view of one embodiment of a catalytic differential calorimetric sensor having a silicon frame 40 with two membranes 44 and 45 with temperature measuring layers 48 and 49 placed on top of the membrane. The temperature measuring layers are covered by a passivation layer 41. A catalytic layer 46 is placed on top of membrane 45. The temperature measuring layer 49 on membrane 44 is used to measure the temperature of the surrounding gas, while the temperature measuring layer on membrane 45 measures the additional heat generated by the catalytic layer. Both membranes are thermally insulated from each other, because both membranes have a low thermal conductivity. A cross-sectional view of the sensor of FIG. 2 taken along lines 4–4 is shown in FIG. 3. The various methods of operating differential calorimetric sensors are known and have been described in, for example, CALORIMETRY FUNDAMENTALS AND PRACTICE by W. Hemminger (1984), herein incorporated by reference.

The membranes 44 and 45 can be made of silicon nitride. The preferred embodiment includes membranes made of a composite of silicon nitride and silicon oxide layers, most preferably silicon nitride, silicon oxide and silicon nitride layers.

Aluminum oxide can be deposited on top of the membrane structure to improve the adhesive properties of the catalytic layer on the membrane. The resultant membranes have a low thermal conductivity and are tensile so they stay flat over a wide temperature range without buckling.

Although microfabricated catalytic microcalorimeters (FIGS. 2 and 3) are known, the present invention provides a chemical and more effective means of fabrication using the sol-gel process. Metals are traditionally loaded on the membrane by sputtering; however, this technique can produce only a limited number of active sites for catalytic oxidization of the combustible gas molecules. This limited number of active catalytic sites might reduce the sensitivity of a catalytic calorimetric gas sensor. To increase the sensitivity and durability of the sensor for automotive applications, this invention describes sol-gel methods which increase the number of catalytic sites without increasing the size of the device. The number of catalytic sites are increased by the use of sol-gel processed alumina/silica based materials which provide a high-surface area washcoat having controlled porosity with narrow pore-size distribution.

In addition to the sol-gel processed washcoat, the present invention discloses a method to maximize deposition of the catalytically active metal particles in the pores of the washcoat. This method reduces agglomeration of the metal particles available for catalytic reactions. Accordingly, the present invention directed efforts to preparing controlled, small metal particles, using a technique disclosed by Schmid in Chem. Rev. 92 (1992) 1709–1727. With Schmid's technique, small noble particles were stabilized by small organic molecules such as sulfanilic acid salts. Another method for preparing controlled size catalytically active metals includes impregnation, whereby the particles are prepared on the washcoat itself. These small noble metal particles in conjunction with high-surface area alumina-based membranes provide a substantially larger number of catalytic sites for calorimetric sensors as compared to conventional fabrication routes.

As used herein, the term washcoat refers to the supporting material on which the catalytically active metal particles are loaded. The term substrate refers to the material supporting the temperature measuring layer and the catalytic layer. The substrate is generally a ceramic 30 or a silicon micromachined structure consisting of a silicon frame 40 and membranes 44 and 45.

There are several metals which act as catalytically active metals, including but not limited to Fe, Cu, Co, Cr, Ni, Mn, Zn, Cd and Ag and mixtures thereof; however, the preferred active metals are generally noble metals. Noble metals are preferred in large part due to their stability towards catalyst poisons. Noble metals include but are not limited to platinum, palladium, silver, gold, ruthenium, rhodium, osmium, iridium and mixtures thereof.

In one washcoat embodiment, alumina sols were prepared by hydrolyzing aluminum alkoxides in water followed by peptization in the presence of dilute mineral acid. The sol was concentrated to a gel which was then heated at 250° C. and 600° C. in a nitrogen atmosphere. An alumina washcoat was then prepared from the alumina sols and showed a surface area of 230 m$^2$/g and a pore size of 45 Å.

Another washcoat embodiment includes preparation of alumina/silica washcoats.

Alumina/sicila washcoats were prepared from a mixture of alumina and silica sol which were gelled, dried and aged at 600° C. Silica sol was prepared from Si(EtO)$_4$ in ethanol, water and dilute mineral acid. The resultant alumina/silica washcoat showed a surface area of 390 m$^2$/g and a pore size of 45 Å. In a second experiment the alumina/silica washcoat was prepared by treating an alumina washcoat with a silica sol, resulting in a pore size of between 30 and 40 Å. In another embodiment, alumina/silica materials were prepared from (tBuO)$_3$ Si—O—Al (OR)$_2$, and Al (OR)$_3$ in parent alcohol. These materials also retained a high surface area after aging at 1100° C. in air.

The alumina sol is preferably prepared by Burgraff's method of preparation of supported and unsupported alumina washcoats. Aluminum sec-butoxide is hydrolyzed in water and heated to remove isopropanol. The residue is treated with dilute nitric acid and peptized for sixteen hours to obtain boehemite sol. The surface area of bulk gel derived from boehemite sol and fired to 600° C. is 200 m$^2$/g and pore size is 45 Å. Notably, Burgraff reports a pore size of 60 Å while our experiments yielded a pore size of 45 Å.

The concentration and viscosity of alumina sol is then adjusted to make it suitable for deposition on the substrate or alternatively on one of the two membranes (in FIGS. 2 and 3) of prefabricated wafers by microcapillary device. The amount of liquid dispensed and the wetting characteristics of the fluid to the substrate determine the thickness of the alumina washcoat. In practice, it is difficult to generate very small drops, however, part of the liquid can be removed by suction leaving only a controlled amount of alumina on the substrate. After drying, the sol is slowly heated to 400° C. and cooled to room temperature, leaving a thin supported alumina washcoat on the substrate.

The alumina washcoat, prepared by this method, has low residual stress, is rather uniform with the exception of the border region and retains high surface area and porosity. The thickness of the alumina washcoat can be varied in the 20–100 nm range and a thicker washcoat can be deposited by repeated applications of alumina sol. An advantage of this method is that it results in an alumina washcoat having relative uniformity and thinness which improves thermal contact between the alumina washcoat and the substrate.

Additionally, the ability to make a thin layer using the sol-gel process provides good thermal contact between the catalytic layer and the temperature measuring layer. A thin layer allows the temperature measuring layer to accurately measure the heat produced by the catalytic layer.

The preferred method of metal sol preparation includes the use of either platinum or palladium as the metal of choice to produce particles having a small and controlled size as described by Schmid.

Platinum or palladium sols are prepared by reduction of chloroplatinic or chloropalladic acids in water. The sols are then stabilized by treatment with sodium salt of sulphanilic acid. After concentrating the sols, metal particles are isolated in solid state (particle size 50–200 Å) and redissolved in water. Practically any concentration of metal particles in water yields acceptable results. Metals are then deposited by microcapillary device on the alumina washcoat of the prefabricated device described above. No further processing is necessary, because the organic component is lost when heated to the operating temperature. The uniform small particle size of the metals and the controlled amounts contribute to a large number of catalytic sites on the sensor device.

The catalytic layer that would be utilized would preferably comprise sol-gel processed catalytically active metal particles in combination with a sol-gel processed washcoat. The metal particles can be deposited on the washcoat or mixed with the washcoat. The term "sol-gel processed catalytic layer" includes: 1) a sol-gel processed washcoat together with sol-gel processed catalytically active metal particles; and 2) a sol-gel processed washcoat together with catalytically active metal particles.

The preferred method of providing a washcoat on a substrate, includes a channeled substrate, such as a honeycomb ceramic structure or the like. The disclosure of this method, in the U.S. Pat. No. 5,210,062 disclosed by Nauru et al., herein incorporated by reference, showed that the sol-gel process was suitable for deposition of a washcoat on a catalytic honeycomb substrate. The '062 patent also demonstrated that the sol-gel process reduced alumina buildup in the corners of the channelled substrate, thereby alleviating the back pressure problem which existed prior to the '062 patent.

The method disclosed in the '062 patent comprises first applying a coating of a reactive mixture on the substrate. A reactive mixture is made by combining a certain type of aluminum alkoxide containing hydrolyzable alkoxy groups with water and acid, generally with stirring, wherein a suspension is formed. The aluminum alkoxide useful with this invention has the chemical formula: Al (OR)$_3$, wherein R comprises alkyl group, branched alkyl group, or aryl group having between 3 and 6 carbon atoms. Aluminum alkoxides which may be used in this invention include, but are not limited to, ethoxides, (n-, or iso)propoxides, (n, sec, or tert-) butoxides, or (n, sec, or tert-) amyloxides. The excess coating from the channels can be removed by blowing gas through the channels. The reactive coating is then hydrolyzed with the addition of water. The coating on the substrate is then dried at a temperature suitable to remove water present in the coating, preferably at or below about 100° C. The method also includes calcining the coating, preferably at a temperature greater than about 300° C., most preferably between about 300° and 900° C., to densify the coating and convert it to γ-alumina. The method may additionally comprise repeatedly applying and drying the coating followed by calcining or doing all three steps until a coating of desired surface area is obtained.

The reactive mixture may further comprise other components such as compatible salts of materials like barium and cerum which would also form oxides thereof in the washcoat. The presence of barium oxide and cerium oxide in the washcoat improves the high temperature stability of the washcoat and the oxidation efficiency of the catalytic layer during use.

For the same reasons, the above method provides a more efficient catalyst for combustible sensors. As with catalytic converters, the catalytic layer of the calorimetric sensor should be disposed on the substrate such that the catalytic active sites are maximized, and to provide an unrestricted flow of exhaust gases to pass through the catalytic layer.

In the above preferred method, the substrate is made preferably of a substantially chemically inert, rigid solid material capable of maintaining its shape and strength at high temperatures. The substrate may be metallic or ceramic in nature or a combination thereof. Suitable materials are α-alumina, cordierite, alpha-alumina, and zirconium silicate. The preferred substrate is the honeycomb ceramic structure. The preferred aluminum alkoxide comprises aluminum tris (sec-butoxide) and the preferred solvent is sec-butanol and the preferred sol is alumina/silica.

In sensor applications, it is also desirable to incorporate at least one other metal atom in the aluminum oxide washcoat. For example, the U.S. Pat. No. 5,134,107 issued to Narula, herein incorporated by reference, teaches a method for making single phase lanthanide-aluminum-oxide materials. Research has shown that when employing aluminum oxide materials as a catalyst washcoat it is desirable to include lanthanum or cerium atoms or both in the aluminum oxide matrix. Incorporating either or both of those metal atoms in the aluminum matrix tends to prevent structural changes that occur in unstabilized γ-alumina at high temperatures, which would tamper with the efficiency of a catalytic sensor. When using sol-gel techniques to make the alumina material, these other metal atoms are added by co-hydrolyzing one or more metal-alkoxides with aluminum alkoxide.

Prior to the '107 patent, such alkoxides when combined in water hydrolyzed, resulting in a mixture of hydroxides. The undesirable final product of such a mixture comprises a non-uniform 2-phase distribution of metal oxide in an aluminum oxide matrix. To overcome these disadvantages, the '107 patent teaches a method which comprises reacting, according to sol-gel techniques, water and heterobimetallic alkoxides comprising tribis(2-propanolato) alumina) hexakis-(2-propanolato))]lanthanide represented by the general chemical formula $Ln[Al(OPri)_4]_3$, Ln being a lanthanide. Lanthanide is meant to include the members of the lanthanide series of the periodic table such as lanthanum and cerium.

The lanthanide-aluminum-oxide materials according to the present invention are made from single phase sols. The sol may be made by forming a reaction mixture of the heterobimetallic alkoxides with water, and adding acid to the reaction mixture to form a sol. Acids employed embodiments of the present invention may be selected from any organic and inorganic acids which may include, but are not limited to, nitric, hydrochloric, sulfuric, acetic and propionic acid. Alcohol is generally employed as a solvent for the alkoxide prior to it being combined with water. Alcohols which may be broadly employed according to embodiments of the present invention include 2-propanol, n-butanol and sec-butanol, with 2 propanol being preferred. The preferred heterobimetallic peroxide is tris [(bis2-propanolato) alumina)hexakis(α-)2-propanolato))] lanthanum. The sol is preferably stabilized by maintaining the reaction mixture for a time and a temperature sufficient to form a stable sol. A stable sol is one that maintains its sol properties and does not experience any substantial gelling when exposed to air or moisture for a significant period of time, e.g., months.

To form a washcoat, the sol is coated on the substrate and then the coating is dried and subsequently calcined at an elevated temperature. Generally calcination is carried out at a temperature above 300° C., preferably between about 300° C. and 900° C. to form a lanthanide-aluminum-oxide material.

Rather than forming a gel from the sol above, gels may be made more directly from lanthanum aluminum alkoxide. For example, the addition of a wet alcohol, generally meant to be one containing more than six equivalents of water, to a solution of the alkoxide in an alcohol at room temperature results in gel formation instantaneously at the contact layer. These sol-gel techniques may also be employed to make aluminum materials comprising more than one lanthanide as a single phase material.

Further, the U.S. Pat. 5,234,881 issued to Narula et al., herein incorporated by reference, discloses a method of making binary lanthanum-palladium oxides useful as an automotive exhaust catalyst washcoat at high temperatures. The teachings of the '881 patent can be readily applied to catalytic sensors.

Prior to the '881 patent efforts to deposit the binary lanthanum-palladium oxide catalysts from their suspension in water followed by sintering resulted in the loss of lanthanum-palladium-oxides. The above-problem was solved in the '881 patent by depositing such oxides from their suspension in an alumina sol on a honeycomb substrate precoated with a commercial washcoat such as γ-alumina. The alumina sol for this purpose can be readily prepared by hydrolyzing aluminum sec-butoxide in water at 70° to 90° C., boiling off sec-butanol at 90°0 C. and acidifying. Two different samples were made by suspending the individual binary oxides ($La_2Pd_2O_5$ or $La_4PdO_7$) in such sols in depositing such suspension onto catalyst substrate, such as monolithic cellular cordierite, which has been previously coated with a commercial washcoat such as γ-alumina. On drying, alumina sol forms a gel and traps the particles of the binary lanthanum-palladium-oxide. The catalyst is then sintered, preferably at 600° C.

For the '881 patent other suitable sols such as $SiO_2$, $TiO_2$ and $ZrO_2$ can be substituted for an alumina sol, $Al_2O$.

Alumina sols were also prepared in the '881 patent by hydrolyzing aluminum alkoxide (eg. $Al(OR_3)$ in water followed by peptization in the presence of diluted mineral acid. The sol was then concentrated to a gel which was heated at between 250° C. and 600°0 C. in a nitrogen atmosphere. Alumina/silica washcoats were prepared for a mixture of alumina sol and silica sol which is obtained from $Si(ETO)_4$ in ethanol, water, and diluted mineral acid. A sample of alumina/silica washcoat was then made with uniform pore size around 45 Å and 390 $m^2/g$.

Further, the sol-gel processed washcoat, can also include as the catalytically active metal, transition-metals. When tested experimentally, silver-containing sol, such as $AgNO_3$ which is water soluble was dissolved in distilled water. The silver solution was then used to impregnate the sol-gel washcoat. The ratio of the silver amount to the sol-gel weight was dependent on the desired silver loading on the sol-gel washcoat. After the impregnation, the material was dried up to 120° C. and then heated in air inside a furnace of 500° to 600° C. for four hours.

Additionally, the present invention's preferred method for fabricating a sensitivity enhanced calorimetric device, includes using silicon-micromachining. Silicon micromachining offers the capability of fabricating devices with low power consumption at potentially lower manufacturing costs. A micromachined device can also have a faster response time because the membrane temperature measuring layer and the catalytic layer have a smaller thermal mass than conventional calorimetric devices.

The preferred embodiment includes fabrication of a silicon micromachined differential microcalorimeter. To improve the detection limit of the sensor the temperature rise is preferably measured differentially by adding a second element with thermal characteristics identical to those of the temperature measuring device, but without a catalytic layer.

The resistances of the two elements are represented by the following equation:

$$R_{catalytic}=R_o[1+\alpha(T+\Delta T_{comb})]$$

$$R_{reference}=R_o[1+\alpha T]$$

with $R_o$ the resistance at 0° C., $\alpha$ the temperature coefficient of resistance, T the temperature of operation in ° C. and $\Delta T_{comb}$ the rise in temperature caused by the oxidation of combustible gases on the catalytic layer, $\Delta T_{comb}$ is given by:

$$\Delta T_{comb}=(R_{catalytic}-R_{reference})/\Delta R_o=\Delta R/\alpha R_o$$

with $\Delta T_{comb}/1000$ ppm of combustible gas defined as the sensitivity of the sensor.

FIG. 2 shows a perspective view and FIG. 3 shows a schematic cross-sectional diagram of one of the device configurations fabricated and studied. Two thin-film resistors are fabricated on two micromachined membranes of low thermal conductivity, and one is covered by a catalytic layer. For simplicity, no heater was incorporated in the design and the devices were heated externally.

The average temperature rise in a microcalorimeter is dictated by the balance of heat produced by the chemical reaction and the heat lost to the environment. In order to maximize the detection limit of the sensor, effects such as the reactant mass transfer, the reaction kinetics at the catalyst, the heat loss by conduction/convection to the ambient gas and by conduction to the substrate, thermal fluctuations in the environment, and the electrical characteristics of the thermometer must all be taken into account.

The key elements of a Si-based microcalorimeter are the catalytic layer, the temperature measuring layer, the heater, and the supporting structure or substrate for all of the previous elements. The substrate consists of a bulk silicon frame with either a membrane layer or a more complex plate/teeter element which in both cases are obtained by etching the underlying bulk silicon frame. The membrane or plate/teeter acts as a support for the temperature measuring layer. Multiple silicon dies can be fabricated from a single silicon wafer. The membrane or plate/teeter should have a small thermal mass for fast response time, but must be mechanically robust to support the temperature measuring layer and the catalytic layer and survive temperature cycling, pressure shocks, water mist and small particle impingement. It should also be configured in such a way as to minimize the heat loss to the silicon frame and to the ambient gas for increased sensitivity. The catalytic layer should have a large specific surface area for the device to operate in mass-transport limited regime. This surface area is achieved by using sol-gel processed alumina-silica washcoat and/or sol-gel processed catalytically active metal particles.

Additionally, good thermal contact between the catalytic layer and the underlying temperature measuring layer is also important for increased sensitivity. The catalytic layer should not substantially change the thermal characteristics of the membrane, otherwise the sensor temperature compensation may be compromised. For greater sensitivity, the temperature measuring layer should mainly measure the central region of the membrane where the temperature rise due to the reaction is the largest, without substantially contributing to conductive heat loss. A thin-film resistor with stable resistance and temperature coefficient of resistance (TCR) is desirable as the temperature measuring layer. The film resistor is patterned as a winding element to increase its resistance (i.e., the output signal) and distribute the stress induced by the thermal mismatch with the membrane.

There are three ways to process the sol-gel catalytic layer. One method includes using a micro syringe to deposit the catalytic layer onto the membrane. With this method, the catalytic layer is deposited to create catalytic active sites specifically at the desired locations. Although this technique provides accurate deposition of the catalytic layer, this technique may not be suitable for mass manufacturing.

A second method involves dipping the silicon wafer into a sol-gel solution to coat the silicon die with a sol-gel processed catalytic layer. This second method is preferred as it provides a controllable and efficient method to batch fabricate catalytic calorimetric gas sensors in a way that is compatible with silicon micromachined structures. The thickness of the catalytic layer can be readily controlled by varying the speed with which the silicon wafer is immersed and removed from the sol-gel solution. This dipping method further requires removal of the sol-gel catalytic layer from specific areas to create the catalytic active sites at the specific desired locations. Selective removal of the catalytic layer can be effectuated in two ways. One involves fabricating a mask on the silicon wafer and placing the mask over the substrate which is then followed by etching away the sol-gel catalytic layer from the undesired locations. The second involves heating the catalytic layer by resistive heating of the membrane on which a catalytic active layer is desired such that the solvents within the sol-gel catalytic layer burn off, resulting in the affixation of the sol-gel catalytic layer in the desired areas. This step is then followed by washing the sol-gel catalytic layer with a solvent to strip the remaining sol-gel solution from the catalytic layer. An acid solvent could strip the solution from the undesired locations. The result in either case is a silicon wafer having a sol-gel processed catalytic layer selectively placed thereon that is easily reproducible. At this time, the preferred method includes dipping the silicon wafer and then etching away the sol-gel solution from the undesired locations.

With the preferred method of fabricating a silicon microcalorimeter, the membrane is deposited first on a silicon wafer, 100 mm in diameter, 400 $\mu$m thick. The membrane is in total preferably between 500–1000 nm, such that it is mechanically stable while being thin enough to prevent loss of heat by thermal conduction through the substrate. Either a 0.6 $\mu$m thick layer of low-stress, low pressure chemical vapor deposition (LPCVD) silicon nitride, or a composite of plasma enhanced chemical vapor deposition (PECVD) silicon oxide/nitride layers (about 0.5 $\mu$m and 0.1 $\mu$m, respectively) deposited over 0.1 $\mu$m of LPCVD nitride can be used. After annealing at 600° C., the latter composite layer has a small residual stress (tensile) of about $6 \times 10^8$ dynes/cm$^2$, the compressive state of the oxide being compensated by the tensile nitride. A Pt film resistance thermometer, 100 nm thick, is sputter deposited. The film resistors, acting as temperature measuring devices and/or heaters, are delineated by lithography and wet etching. After annealing the Pt resistors at 500° C. in nitrogen to stabilize their resistance and temperature coefficient of resistance (TCR), the wafers are coated with 0.2–0.3 $\mu$m of PECVD silicon nitride for passivation and annealed at 500° C. The passivation is then removed on the contact pads with plasma etching. While defining the opening for the contact pads, an etch-mask pattern is also defined on the back side of the wafer using a double-sided aligner. A 30% aqueous solution of KOH at 80° C. is used to completely etch the silicon underneath the membrane. The membrane has sufficient mechanical strength to allow the wafer to be diced with a diamond saw. For ease of handling, a die size of 7×7 mm$^2$ is used, although only a 3.5×3.5 mm$^2$ area is needed for the device with the smallest membrane.

While the best mode for carrying out the invention has been described in detail, those familiar with the art to which this invention relates will recognize various alternative designs and embodiments for practicing the invention as defined by the following claims.

We claim:

1. A differential gas combustible microcalorimeter sensor comprising:
   a substrate which comprises:
      a silicon frame,
      a first reference membrane disposed on said silicon frame, and
      a second membrane disposed on said silicon frame, said second membrane being positioned such that said second membrane is thermally isolated from said first reference membrane;
   a first and second temperature measuring devices, the first temperature measuring device being disposed on said first reference membrane and the second temperature measuring device being disposed on said second membrane; and
   a sol-gel processed catalytic layer disposed on said second temperature measuring device, wherein said first and second temperature measuring devices provide a measurement of the additional heat generated by the catalytic layer to provide a means of calculating the temperature fluctuation in a combustible gas that comes into contact with the sensor.

2. The sensor of claim 1, wherein said sol-gel processed catalytic layer comprises:
   a sol-gel processed washcoat, wherein the washcoat is selected from the group consisting of alumina, silica and mixtures thereof; and
   a plurality of sol-gel processed catalytically active metal particles deposited on said sol-gel washcoat.

3. The sensor of claim 2, wherein said catalytically active metal particles are noble metals selected from the group consisting of platinum, palladium, silver, gold, ruthenium, rhodium, osmium, iridium, and mixtures thereof.

4. The sensor of claim 1, wherein said sol-gel processed catalytic layer comprises:
   a sol-gel processed washcoat, wherein said washcoat is selected from the group consisting of alumina, silica and mixtures thereof; and
   a plurality of catalytically active metal particles deposited on said sol-gel processed washcoat.

5. The sensor of claim 4, wherein said catalytically active metal particles are noble metals selected from the group consisting of platinum, palladium, silver, gold, ruthenium, rhodium, osmium, iridium, and mixtures thereof.

* * * * *